United States Patent [19]
Scheiblich et al.

[11] Patent Number: 6,130,188
[45] Date of Patent: Oct. 10, 2000

[54] HERBICIDAL PYRIDINE COMPOUNDS

[75] Inventors: Stefan Scheiblich; Thomas Maier, both of Mainz; Helmut Siegfried Baltruschat, Schweppenhausen; Thomas Hoellmueller, Gau-Algesheim, all of Germany

[73] Assignee: American Cyanamid Company, Madison, N.J.

[21] Appl. No.: 09/287,898

[22] Filed: Apr. 7, 1999

Related U.S. Application Data

[60] Provisional application No. 60/084,282, May 5, 1998.
[51] Int. Cl.$^7$ .................... C07D 401/12; A01N 43/44
[52] U.S. Cl. .................... 504/253; 504/251; 504/256; 546/276.1; 546/280.4; 546/296
[58] Field of Search .................... 546/276.1; 504/253

[56] References Cited

FOREIGN PATENT DOCUMENTS

| | | |
|---|---|---|
| 0109751 | 10/1983 | European Pat. Off. . |
| 223 406 | 5/1987 | European Pat. Off. . |
| 227 045 | 7/1987 | European Pat. Off. . |
| 272 533 | 6/1988 | European Pat. Off. . |
| WO94/22833 | 10/1994 | WIPO . |

*Primary Examiner*—Jane Fan
*Attorney, Agent, or Firm*—Joseph M. Mazzarese

[57] ABSTRACT

The novel compounds of formula I:

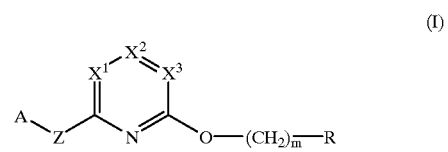

wherein R, A, $X^1$, $X^2$, $X^3$, Z and m have the meaning given in claim 1, and the agronomically acceptable salts or N-oxides thereof, and herbicidal compositions containing such compounds as active ingredients.

8 Claims, No Drawings

HERBICIDAL PYRIDINE COMPOUNDS

The applciation claims benefit of Provisional application 60/084,282 filed May 5, 1998.

BACKGROUND OF THE INVENTION

Selective herbicidal compounds play an important role in agriculture and related fields. Growers seek herbicides that kill pest plants, but do not reduce crop yield. Although numerous selective herbicides have been described, there is nevertheless a considerable interest in new compounds having a superior or different activities, because the known herbicidal compounds either are not suitable for application in certain crops, or are not sufficiently selective.

Selective herbicides the active ingredients of which are pyridine derivatives, and particularly 2,6-substituted pyridines, are known from WO 94/22833.

The European patent application EP 0 109 751 discloses herbicidal 6-difluormethoxy- and 6-tetrafluorethoxy-2-phenyloxypyridines.

However, 2,6-disubstituted pyridine derivatives in which a haloalkylmethoxy or a haloalkenyloxy group is attached to the pyridine group in the 2-position have not yet been described.

SUMMARY OF THE INVENTION

The present invention provides novel compounds of the general formula (I)

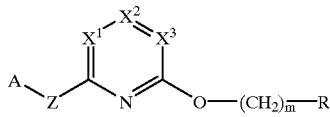
(I)

wherein one of the groups $X^1$, $X^2$ and $X^3$ represents N or $CR^1$ and the others represent $CR^1$;
$R^1$ each independently represent a hydrogen or halogen atom or an optionally substituted alkyl, alkenyl, alkinyl, alkoxy, alkoxyalkyl, alkoxyalkoxy, group or a haloalkyl, haloalkoxy, cyano, nitro or $SF_5$ group; or $-S(O)_p-R^1$, in which p is 0, 1 or 2, and $R^1$ represents an alkyl or haloalkyl group; or $-NR^2R^3$, in which $R^2$ and $R^3$ each independently represent a hydrogen atom, an alkyl, alkenyl, aralkyl or aryl group, or $R^4O-CY$-, in which $R^4$ represents an alkyl group, and Y represents O or S;
A represents an optionally substituted aryl group, an optionally substituted 5- or 6- membered nitrogen-containing heteroaromatic group or an optionally substituted thienyl group;
R represents an optionally substituted haloalkyl or haloalkenyl group; m is 0, 1, 2 or 3;
Z represents an oxygen or sulfur atom, and the agronomically acceptable salts or N-oxides thereof;
with the proviso that R represents an optionally substituted haloalkenyl group, in the event that m is 0.

The new compounds show an excellent selective herbicidal activity in various crops.

It is an object of the present invention to provide novel, selective herbicidal compounds.

It is also an object of the invention to provide methods for controlling undesired plant growth by contacting said plants with a herbicidally effective amount of the new compounds.

It is another object of the invention to provide selective herbicidal compositions containing the new compounds as active ingredients.

These and other objects and features of the invention will be more apparent from the detailed description set forth hereinbelow, and from the appended claims.

DETAILED DESCRIPTION OF THE PREFERRED EMBODIMENTS

It has surprisingly been found that the compounds of the general formula (I)

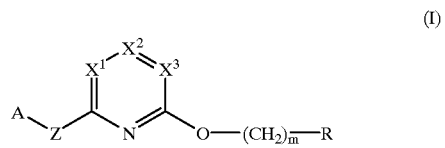
(I)

wherein
A, R, m, $X^1$ through $X^3$ and Z are as described above and the agronomically acceptable salts or N-oxides thereof, show considerable herbicidal activity and high selectivity in certain crops, such as maize and rice, in pre- and post-emergence applications on both broadleaf and grassy weed species.

In the definitions of the new compounds, an aryl group is suitably an optionally substituted phenyl or naphthyl group. Within the definition of A, the 5-or 6-membered nitrogen-containing heteroaryl groups comprise optionally substituted 5- or 6-membered heterocycles containing one or more nitrogen and/or oxygen and/or sulphur atoms, 1 to 3 nitrogen atoms being preferred. Examples of such groups are pyrazolyl, imidazolyl, triazolyl, tetrazolyl, pyridyl, pyrazinyl, pyrimidyl, pyridazinyl, isoxazolyl, isothiazolyl and triazinyl groups. A also includes optionally substituted thienyl groups.

Generally, in compounds of the present invention, alkyl, alkenyl or alkynyl groups, unless otherwise specified, may be linear or branched and may contain up to 12, preferably up to 6, and most preferably up to 4, carbon atoms. Examples of such groups are methyl, ethyl, propyl, vinyl, allyl, propargyl, isopropyl, butyl, isobutyl and tertiary-butyl groups. The alkyl portion of a haloalkyl, haloalkenyl, haloalkoxy, alkylthio, haloalkylthio or alkoxy group suitably has up to 12 carbon atoms, preferably up to 6, and most preferably up to 4, carbon atoms. The double bond of the alkenyl and haloalkenyl groups is as a rule located in the 1- or 2-position with respect to the point of their attachment. The number of carbon atoms in the alkoxyalkyl, alkoxyalkoxy or dialkoxyalkyl groups is up to 6, preferably up to 4, e.g. methoxymethyl, methoxymethoxy, methoxyethyl, ethoxymethyl, ethoxyethoxy, dimethoxymethyl.

"Halogen" means a fluorine, chlorine, bromine or iodine atom, preferably fluorine, chlorine or bromine.

m is preferably 1 or 2.

Haloalkyl, haloalkenyl, haloalkylthio and haloalkoxy are preferably mono-, di-, tri-, tetra- or pentafluoroalkyl, -alkenyl, -alkylthio and -alkoxy, or monochloro- or dichloroalkenyl, or monobromoalkenyl, especially preferred are trifluoromethyl, tetrafluoroethyl, pentafluoroethyl, octafluorobutyl, 3,3,3-trifluoroprop-1-enyl, 2-methyl-3,3,3-trifluoroprop-1-enyl, 4,4,4-trifluorobut-1-enyl, 1,2-difluorobuta-1,3-dienyl, 1 - or 2-chlorovinyl, 2,2-dichlorovinyl, 1,2-dichlorovinyl, 1,2-dichloroprop-1-enyl, 3,3,3-trichloroprop-1-enyl, 2-bromoallyl, difluoromethoxy, trifluoromethylthio, difluoromethylthio and trifluoromethoxy.

When any groups are designated as being optionally substituted, the substituent groups which are optionally present may be any of those customarily employed in the modification and/or development of pesticidal compounds and are especially substituents that maintain or enhance the herbicidal activity associated with the compounds of the present invention, or influence persistence of action, soil or plant penetration, or any other desirable property of such herbicidal compounds.

There may be one or more of the same or different substituents present in each part of the molecules. In relation to moieties defined above as comprising an optionally substituted alkyl group, including alkyl parts of haloalkyl, alkoxy, alkylthio, haloalkoxy, haloalkylthio, alkylamino and dialkylamino groups, specific examples of such substituents include phenyl, halogen atoms, nitro, cyano, hydroxyl, $C_{1-4}$-alkoxy, $C_{1-4}$-haloalkoxy, $C_{1-4}$-haloalkylthio and $C_{1-4}$-alkoxycarbonyl groups.

In relation to moieties defined above as comprising an optionally substituted aryl or heteroaryl group, optional substituents include halogen, nitro, cyano, amino, hydroxyl, $C_{1-4}$-alkyl, $C_{1-4}$-alkoxy, $C_{1-4}$-haloalkyl, $C_{1-4}$-haloalkylthio, $C_{1-4}$-haloalkoxy, $C_{2-4}$ haloalkenyl, and halosulfanyl groups having 1–5 halogen atoms, such as $SF_5$. From 1 to 5 substituents may be present, 1 to 2 substituents being preferred. Typically, haloalkyl, haloalkenyl, haloalkoxy and haloalkylthio groups are trifluoromethyl, difluoromethoxy, trifluoromethoxy, difluoromethylthio and trifluoromethylthio groups.

Preferred compounds within the above definitions are those in which A represents a phenyl, pyridyl or pyrazolyl group, unsubstituted or substituted by one or more identical or different substituents selected from halogen atoms, alkyl, alkoxy, haloalkyl, haloalkylthio, haloalkoxy and pentahalosulfanyl groups. Preferably, at least one substituent is attached in the 3-position with respect to the carbon atom attached to the group Z. Most preferred A is a group of formula A,

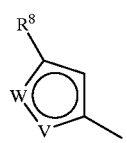

(A)

in which $R^8$ represents a halogen atom, or an alkyl, alkoxy, haloalkyl, haloalkylthio, haloalkoxy or pentahalosulfanyl group;

V represents CH or NCH.;

W represents N, S, N-CH or CH-CH.

$X^1$ and $X^3$ preferably represent CH or C-Halogen, in particular C-F, and $X^2$ represents $CR^1$, in which $R^1$ has the meaning given and is preferably alkyl or alkoxy.

Preferred embodiments of the present invention are:

(a) A compound of formula I, wherein Z represents an oxygen atom.

(b) A compound of formula I, wherein R represents a group of formula 1:

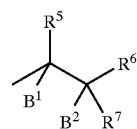

(1)

(c) in which $R^5$ through $R^7$ represent a hydrogen or halogen atom or an optionally substituted alkyl or alkoxy group; at least one of which being a halogen atom, a haloalkyl or haloalkoxy group; in particular a fluoro, chloro or bromo atom or a $C_{1-3}$ haloalkyl group, and $B^1$ and $B^2$ each independently represent a hydrogen or halogen atom or taken together a double bond, in particular wherein R represents a haloalkyl or haloalkenyl group selected from trifluoromethyl, tetrafluoroethyl, pentafluoroethyl, octafluorobutyl, 3,3,3-trifluoroprop-1-enyl, 2-methyl-3,3,3-trifluoroprop-1-enyl, 4,4,4-trifluorobut-1-enyl, 1,2-difluorobuta-1,3-dienyl, 1- or 2-chlorovinyl, 2,2-dichlorovinyl, 1,2-dichlorovinyl, 1,2-dichloroprop-1-enyl, 3,3,3-trichloroprop-1-enyl and 2-bromoallyl. The double bond of the haloalkenyl group has preferably the (E)-configuration.

(d) A compound of formula 1, wherein A represents a group selected from optionally substituted phenyl, pyridyl, thienyl and pyrazolyl, preferably wherein A represents a group selected from the formulae (2), (3), (4), and (5):

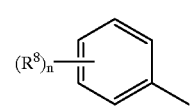

(2)

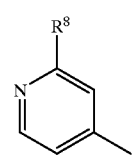

(3)

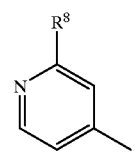

(4)

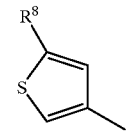

(5)

wherein $R^5$ each independently represents a halogen atom or an optionally substituted alkyl group;

$R^9$ represents an alkyl group; and n represents an integer of 1 to 5, in particular wherein A represents one of the groups 2', 3', 4' or 5':

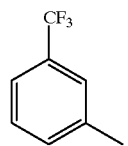
(2')

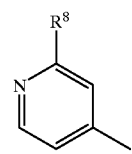
(3')

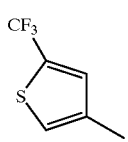
(4')

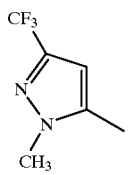
(5')

where R⁸ is a chlorine atom, a trifluoromethyl or a difluoromethoxy group.

(e) A compound of formula IA

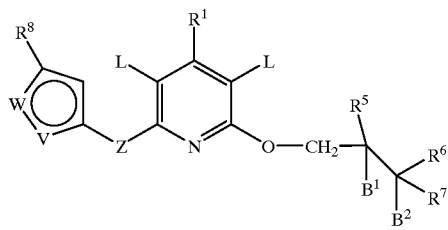
(IA)

wherein $R^1$, $R^5$, $R^6$, $R^7$, $R^8$, $B^1$, $B^2$ and Z have the meaning given above;

L represents a hydrogen or fluorine atom;

W-V represents N-CH, S-CH, N-CH-CH, CH-CH-CH or N-NCH₃;

(f) A compound according to claim 1 selected from the group consisting of 2-(1-methyl-3-trifluoromethylpyrazol-5-yloxy)-6-(2,2,3,3-tetrafluoropropyloxy)-4-methylpyridine; 2-(1-methyl-3-trifluoromethylpyrazol-5-yloxy)-6-(4,4,4-trifluorobut-2-enyloxy)-4-methylpyridine; 2-(1-methyl-3-trifluoromethylpyrazol-5-yloxy)-6-(3-bromobut-3-enyloxy)-4-methylpyridine; 2-(5-trifluoromethylthien-3-yloxy)-6-(2,2,3,3-tetrafluoropropyloxy)-4-methylpyridine; 2-(5-trifluoromethylthien-3-yloxy)-6-(4,4,4-trifluorobut-2-enyloxy)-4-methylpyridine; 2-(3-trifluoromethylphenyloxy)-6-(2,2,3,3-tetrafluoropropyloxy)-4-methylpyridine; 2-(3-trifluoromethylphenyloxy)-6-(4,4,4-trifluorobut-2-enyloxy)-4-methylpyridine; 2-(1-methyl-3-trifluoromethylpyrazol-5-yloxy)-6-(4,4,4-trifluorobut-1-enyloxy)-4-methyl pyridine; 2-(1-methyl-3-trifluoromethylpyrazol-5-yloxy)-6-(3-chloroprop-2-enyloxy)-4-methylpyridine; 2-(1-methyl-3-trifluoromethylpyrazol-5-yloxy)-6-(2,2,3,3-tetrafluoropropyloxy)-4-methoxy pyridine; 4-cyano-6-(4,4,4-trifluorobut-2-enyloxy)-2-(5-trifluoromethylthienyl-3-oxy)pyridine; 4-cyano-6-(3,3-dichloroprop-2-enyloxy)-2-(5-trifluoromethylthienyl-3-oxy)pyridine; 4-cyano-6-(3-chlorobut-2-enyloxy)-2-(5-trifluoromethylthienyl-3-oxy)pyridine; 6-(3-chlorobut-2-enyloxy)-2-(3-trifluoromethylphenyloxy)-4-methylpyridine; 2-(1-methyl-3-trifluoromethylpyrazol-5-yloxy)-6-(3-methyl-4,4,4-trifluorobutyloxy)-4-methylpyridine; 2-(1-methyl-3-trifluoromethylpyrazol-5-yloxy)-6-(2-methyl-4,4,4-trifluorobutyloxy)-4-methylpyridine; 6-(3,3-dichloroprop-2-enyloxy)-3,5-difluoro-2-(1-methyl-3-trifluoromethylpyrazol-5-yloxy)-4-methylpyridine; 3,5-difluoro-6-(3-chloroprop-2-enyloxy)-2-(1-methyl-3-trifluoromethylpyrazol-5-yloxy)-4-methylpyridine; 3,5-difluoro-6-(3-chlorobut-2-enyloxy)-2-(1-methyl-3-trifluoromethylpyrazol-5-yloxy)-4-methylpyridine; 6-(2-chloroprop-2-enyloxy)-2-(1-methyl-3-trifluoromethylpyrazol-5-yloxy)-4-methylpyridine; 6-(4-chlorobut-2-enyloxy)-2-(1-methyl-3-trifluoromethylpyrazol-5-yloxy)-4-methylpyridine; 2-(1-methyl-3-trifluoromethylpyrazol-5-yloxy)-4-methyl-6-(3,4,4-trifluorobut-3-enyloxy)-pyridine; and 6-(4,4-difluoro-3-methylbut-3-enyloxy)-2-(1-methyl-3-trifluoromethylpyrazol-5-yloxy)-4-methylpyridine.

The compounds of this invention can be prepared according to the following methods:

Method (A): reacting a respective compound of the general formula II

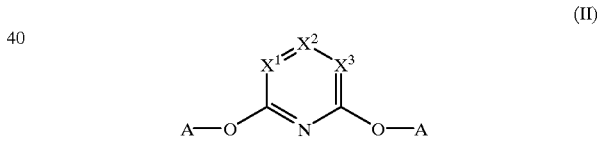
(II)

in which $X^1$, $X^2$, $X^3$ and A have the meaning given, with a compound of general formula III,

(III)

in which R and m have the meaning given, or a metal salt thereof.

Method (B): Alternatively, a compound of formula IV,

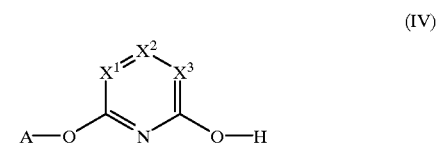
(IV)

in which A and $X^1$ through $X^3$ are as defined above, is reacted with a compound of formula III in the presence of a dehydrating agent, preferably in the presence of triphenylphosphine and diethyl azodicarboxylate (Mitsonobu method).

Method (C): Alternative a compound of formula IV,

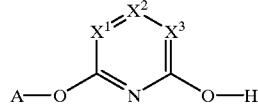

(IV)

in which A and $X^1$ through $X^3$ are as defined above, is reacted with a compound of formula V,

(V)

in which LG represents a suitable leaving group, such as a halogen atom or a tosylate or mesylate group, in the presence of a base.

Method (D): Alternatively, a compound of formula VI,

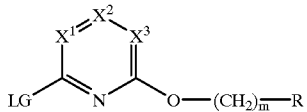

(VI)

in which R, m and $X^1$ through $X^3$ are as defined above, and LG denotes a 20 suitable leaving group, is reacted with a compound of formula VII,

(VI)

in which A has the meaning given, in the presence of a base.

The N-oxides of the compounds of formula I can be prepared according to known methods, particularly with the aid of the following methods:

Method (E): A compound of formula VIII,

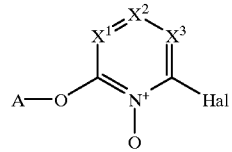

(VIII)

in which A and $X^1$ through $X^3$ are as defined above and Hal is a halogen atom, is reacted with a compound of formula III1 in the presence of a base. The compounds of formula VIII can be prepared by reaction of 2,6-dihalopyridine N-oxide with a compound of formula VII in the presence of a base.

These reactions are conveniently carried out in an organic solvent at elevated temperature. Generally, any polar organic solvent is suitable, e.g. dimethylformamide, tetrahydrofuran, sulfolane, pyridines. The metal salts of the compounds of formula III are suitably alkali metal salts, preferably the sodium or potassium salts. In some cases, the presence of copper salts has been found to be useful.

The metal salts are conveniently generated by reaction of the compound of formula III with a suitable metal base, a metal carbonate or hydride.

The prepared compounds of formula I may be isolated and purified using conventional methods and techniques.

The starting compounds for the preparation of compounds of this invention are either known from WO 94/22833 or can be prepared according to known methods.

The following acids are suitable for the preparation of the agronomically acceptable salts of the compounds of formula I: hydrohalides like hydrochloric or hydrobromic acid, phosphoric acid, nitric acid, sulfuric acid, mono- or bifunctional carboxylic acids and hydroxycarboxylic acids like acetic acid, maleic acid, succinic acid, fumaric acid, citric acid, salicylic acid, sorbic acid or lactic acid and sulfonic acids like p-toluenesulfonic acid or naphthalene-1,5-diyl-disulfonic acid. The agronomically acceptable salts of the compounds of formula I are prepared according to conventional salt formation procedures, for example by dilution of a compound of formula I in a suitable organic solvent, addition of an acid and isolation of the salt formed by, for example, filtration and optional purification by washing with an inert solvent.

The compounds of general formula I have been found to have herbicidal activity. Accordingly, the invention further provides a herbicidal composition which comprises an active ingredient, which includes at least one compound of formula I as defined above, and one or more carriers. A method of making such a composition is also provided which comprises bringing a compound of formula I as defined above into association with the carrier(s). Such a composition may contain a single active ingredient or a mixture of several active ingredients of the present invention. It is also envisaged that different isomers or mixtures of isomers may have different levels or spectra of activity and thus compositions may comprise individual isomers or mixtures of isomers.

A composition according to the invention preferably contains from 0.5% to 95% by weight (w/w) of active ingredient.

A carrier in a composition according to the invention is any material with which the active ingredient is formulated to facilitate application to the locus to be treated, which may be, for example, a plant, seed or soil, or to facilitate storage, transport or handling. A carrier may be a solid or a liquid, including material which is normally a gas but which has been compressed to form a liquid.

The compositions may be manufactured into e.g. emulsion concentrates, solutions, oil in water emulsions, wettable powders, soluble powders, suspension concentrates, dusts, granules, water dispersible granules, micro-capsules, gels and other formulation types by well-established procedures. These procedures include intensive mixing and/or milling of the active ingredients with other substances, such as fillers, solvents, solid carriers, surface active compounds (surfactants), and optionally solid and/or liquid auxiliaries and/or adjuvants. The form of application such as spraying, atomizing, dispersing or pouring may be chosen like the compositions according to the desired objectives and the given circumstances.

Solvents may be aromatic hydrocarbons, e.g. Solvesso® 200, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl-2-pyrrolidone, or y-butyrolactone, higher alkyl pyrrolidones, e.g. n-octylpyrrolidone or cyclohexylpyrrolidone, epoxidized plant oil esters, e.g. methylated coconut or soybean oil ester and water. Mixtures of different liquids are often suitable.

Solid carriers, which may be used for dusts, wettable powders, water dispersible granules, or granules, may be mineral fillers, such as calcite, talc, kaolin, montmorillonite or attapulgite. The physical properties may be improved by addition of highly dispersed silica gel or polymers. Carriers for granules may be porous material, e.g. pumice, kaolin, sepiolite, bentonite; non-sorptive carriers may be calcite or sand. Additionally, a multitude of pre-granulated inorganic or organic materials may be used, such as dolomite or crushed plant residues.

Pesticidal compositions are often formulated and transported in a concentrated form which is subsequently diluted by the user before application. The presence of small amounts of a carrier which is a surfactant facilitates this process of dilution. Thus, preferably at least one carrier in a composition according to the invention is a surfactant. For example, the composition may contain at two or more carriers, at least one of which is a surfactant.

Surfactants may be nonionic, anionic, cationic or zwitterionic substances with good dispersing, emulsifying and wetting properties depending on the nature of the compound according to general formula I to be formulated. Surfactants may also mean mixtures of individual surfactants.

The compositions of the invention may for example be formulated as wettable powders, water dispersible granules, dusts, granules, solutions, emulsifiable concentrates, emulsions, suspension concentrates and aerosols. Wettable powders usually contain 5 to 90% w/w of active ingredient and usually contain in addition to solid inert carrier, 3 to 10% wiw of dispersing and wetting agents and, where necessary, 0 to 10% w/w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5 to 10% w/w of active ingredient. Water dispersible granules and granules are usually prepared to have a size between 0.15 mm and 2.0 mm and may be manufactured by a variety of techniques. Generally, these types of granules will contain 0.5 to 90% w/w active ingredient and 0 to 20% w/w of additives such as stabilizer, surfactants, slow release modifiers and binding agents. The so-called "dry flowables" consist of relatively small granules having a relatively high concentration of active ingredient. Emulsifiable concentrates usually contain, in addition to a solvent or a mixture of solvents, 1 to 80% w/v active ingredient, 2 to 20% w/v emulsifiers and 0 to 20% w/v of other additives such as stabilizers, penetrants and corrosion inhibitors. Suspension concentrates are usually milled so as to obtain a stable, non-sedimenting flowable product and usually contain 5 to 75% w/v active ingredient, 0.5 to 15% w/v of dispersing agents, 0.1 to 10% w/v of suspending agents such as protective colloids and thixotropic agents, 0 to 10% w/v of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation and crystalization or as antifreeze agents for water.

Aqueous dispersions and emulsions, for example compositions obtained by diluting the formulated product according to the invention with water, also lie within the scope of the invention.

Of particular interest in enhancing the duration of the protective activity of the compounds of this invention is the use of a carrier which will provide slow release of the pesticidal compounds into the environment of a plant which is to be protected.

The biological activity of the active ingredient can also be increased by including an adjuvant in the spray dilution. An adjuvant is defined here as a substance which can increase the biological activity of an active ingredient but is not itself significantly biologically active. The adjuvant can either be included in the formulation as a coformulant or carrier, or can be added to the spray tank together with the formulation containing the active ingredient.

As a commodity the compositions may preferably be in a concentrated form whereas the end user generally employs diluted compositions. The compositions may be diluted to a concentration down to 0.001% of active ingredient. The doses usually are in the range from 0.01 to 10 kg a.i./ha.

Examples of formulations according to the invention are:

| Emulsion Concentrate (EC) | | |
|---|---|---|
| Active Ingredient | Compound of Example 11 | 30% (w/v) |
| Emulsifier(s) | e.g. Atlox ® 4856 B and Atlox ® 4858 B[1] | 5% (w/v) |
| Solvent | e.g. Shellsol ® A[2] | to 1000 ml |
| Suspension Concentrate (SC) | | |
| Active Ingredient | Compound of Example 11 | 50% (w/v) |
| Dispersing agent | e.g. Soprophor ® FL[3] | 3% (w/v) |
| Antifoaming agent | e.g. Rhodorsil ® 422[3] | 0.2% (w/v) |
| Structure agent | e.g. Kelzan ® S[4] | 0.2% (w/v) |
| Antifreezing agent | e.g. Propylene glycol | 5% (w/v) |
| Biocidal agent | e.g. Proxel ®[5] | 0.1 % (w/v) |
| Water | | to 1000 ml |
| Wettable Powder (WP) | | |
| Active Ingredient | Compound of Example 11 | 60% (w/w) |
| Wetting agent | e.g. Atlox ® 4995[1] | 2% (w/w) |
| Dispersing agent | e.g. Witcosperse ® D-60[6] | 3% (w/w) |
| Carrier/Filler | e.g. Kaolin | 35% (w/w) |
| Water Dispersible Granules | | |
| Active Ingredient | Compound of Example 11 | 50% (w/w) |
| Dispersing/Binding agent | e.g. Witcosperse ® D-450[6] | 8% (w/w) |
| Wetting agent | e.g. Morwet ® EFW[6] | 2% (w/w) |
| Antifoaming agent | e.g. Rhodorsil ® EP 6703[3] | 1% (w/w) |
| Disintegrant | e.g. Agrimer ® ATF[7] | 2% (w/w) |
| Carrier/Filler | e.g. Kaolin | 35% (w/w) |

[1] Product commercially available from ICI Surfactants
[2] Product commercially available from Deutsche Shell AG
[3] Product commercially available from Rhône-Poulenc
[4] Product commercially available from Kelco Co.
[5] Product commercially available from Zeneca
[6] Product commercially available from Witco
[7] Product commercially available from International Speciality Products The compositions of this invention can also comprise other compounds having biological activity, e.g. compounds having similar or complementary pesticidal activity or compounds having plant growth regulating, fungicidalfherbicidal or insecticidal activity. These mixtures of pesticides can have a broader spectrum of activity than the compound of general formula I alone. Furthermore, the other pesticide can have a synergistic effect on the pesticidal activity of the compound of general formula 1.

The active ingredients according to the invention can be employed alone or as formulations in combination with conventional herbicides. Such combinations of at least two herbicides can be included in the formulation or also added in a suitable form with the preparation of the tank mix. For such mixtures at least one of the following known herbicides can be used: ametrydione, metabenzthiazuron, metamitron, metribuzin, 2,4-D, 2,4-DB, 2,4-DP, alachlor, alloxydim, asulam, atrazin, bensulfuron, bentazon, bifenox, bromoxynil, butachlor, chloridazon, chlorimuron, chlorpropham, chlorsulfuron, chlortoluron, cinmethylin, clopyralid, cyanazin, cycloate, cycloxydim, dichlobenil, diclofop, eptame, ethiozin, fenoxaprop, fluazifop, fluometuron, fluridone, fluroxypyr, fomesafen, glyphosate, haloxyfop, hexazinone, imazamethabenz, imazapyr, imazaquin, imazethapyr, ioxynil, isoproturon, lactofen, MCPA, MCPP, mefenacet, metazachlor, metolachlor, metsulfuron, molinate, norflurazon, oryzalin, oxyfluorfen, pendimethalin, picloram, pretilachlor, propachlor, pyridate, quizalofopethyl, sethoxydim, simetryne, terbutryne, thiobencarb, triallate, trifluralin, diflufenican, propanil, triclopyr, dicamba, desmedipham, acetochlor, fluoroglycofen, halosafen, tralkoxydim, amidosulfuron, cinosulfuron, nicosulfuron, pyrazosulfuron, thiameturon, thifensulfuron, triasulfuron, oxasulfuron, azimsulfuron, tribenuron, esprocarb, prosulfocarb, terbutylazin, benfuresate, clomazone, di-methazone, dithiopyr, isoxaben, quinchlorac, qinmerac, sulfosate, cyclosulfamuron, imazamox, imazamethapyr, flamprop-M-methyl, flamprop-M-isopropyl, picolinafen, thiafluamide, isoxaflutole, flurtamone, daimuron, bromobutide, methyldimron, dimethenamid, sulcotrione, sulfentrazone, oxadiargyl, acifluorfen, cafenstrole, carfentrazone, diuron, glufosinate.

Mixtures with other active ingredients like fungicides, insecticides, acaricides, and nematicides are possible.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

EXAMPLE 1

(a) 6-Hydroxy-2-(1-methyl-3-trifluoromethylpyrazol-5-yloxy)-4-methylpyridine

Method A:

A mixture of 2,6-bis(1-methyl-3-trifluoromethylpyrazol-5-yloxy)-4-methylpyridine (prepared according to WO 94/22833; 4.2 g, 10 mmol) and NaOH (1 g, 25 mmol) is heated in DMSO (50 ml) and water (5 ml) for 36 h at 100° C. After cooling, the reaction mixture is diluted with water and acidified with hydrochloric acid. The mixture is diluted with pentane/ethyl acetate (300 ml by volume ration 1/1) and the organic layer is washed 6 times with water. The organic layer is dried with anhydrous magnesium sulfate, filtered and evaporated in vacuo. Purification by flash chromatography (silica gel: pentane/ethyl acetate 8/2 v/v and 7/3 v/v) yields the title compound (1.9 g, 70 % yield) of m.p. 159° C.

Method B

A mixture of 6-benzyloxy-2-(1-methyl-3-trifluoromethylpyrazol-5-yloxy)-4-methylpyridine (prepared according to W094/22833; 34 g, 93 mmol) and catalytic amounts of palladium on carbon is reduced in methanol by hydrogen at ambient temperature. After filtration, the solution is evaporated in vacuo. Treatment of the residue with a mixture of pentane and diisopropyl ether yields the title compound (18.9 g, 74 % yield) of m.p. 159 ° C.

(b) (E)-2-(1-Methyl-3-trifluoromethylpyrazol-5-yloxy)-4-methyl-6-(4,4,4-trifluorobut-2-envioxy)pyridine A mixture of 6-hydroxy-2-(1-methyl-3-trifluoromethylpyrazol-5-yloxy)-4-methylpyridine (0.8 g, 2.93 mmol), 4,4,4-trifluorobut-2-en-1-ol (0.44 g, 3.5 mmol), triphenylphosphine (0.92 g, 3.51 mmol) and diethyl azodicarboxylate (0.61 g, 3.51 mmol) in dry dioxane (3 ml) is stirred for 1.5 h at ambient temperature. The reaction mixture is diluted with pentane/ethyl acetate (by volume ration 1/1) and filtered through a bed of silica gel. The filtrate is washed with water. The organic layer is dried with anhydrous magnesium sulfate, filtered and evaporated in vacuo. Purification by flash chromatography (silica gel: pentane/ethyl acetate 9/1 v/v) yields the title compound (1.11 g, 70 % yield) as an colorless oil.

EXAMPLE 2

2-(1-Methyl-3-trifluoromethylryrazol-5-yloxy)-4-methyl-6-(4,4,4-trifluorobut-1-enyloxy)pyridine To a solution of trimethylsulfoxonium iodide (4.5 g, 20.5 mmol) in DMSO (50 ml) is added NaH (60 % in oil, 0.82 g, 20.5 mmol) and the resulting mixture is stirred for 1 h at ambient temperature. To the resulting solution is added dropwise a solution of (E)-2-(1-methyl-3-trifluoromethylpyrazol-5-yloxy)-4-methyl-6-(4,4,4-trifluorobut-2-enyloxy)pyridine (example 1, 7.1 g,18.6 mmol) at 10° C. After 3 h of stirring at ambient temperature, the dark mixture is hydrolyzed with water (200 ml) and extracted 3 times with diethylether (50 ml). The organic fractions are washed with water, dried over anhydrous magnesium sulfate, filtered and evaporated in vacuo. Purification by flash chromatography (silica gel: pentane/ethyl acetate 9/1 v/v) yields the title compound (0.22 g, 3.1 % yield) of m.p. 56 ° C.

EXAMPLE 3

(E)-2-(1-Methyl-3-trifluoromethylpyrazol-5-yloxy)-4-methyl-6-(3-chloroprop-2-enyloxy)pyridine A mixture of 6-hydroxy-2-(1-methyl-3-trifluoromethylpyrazol-5-yloxy)-4-methylpyridine (0.9 g, 3.3 mmol) and NaH (60 % in oil, 0.16 g, 4 mmol) in acetonitrile (20 ml) and DMF (1 ml) is stirred for 10 min at ambient temperature and (E)-1,3-dichloropropene (0.4 g, 3.6 mmol) is added. After stirring for 60 h at ambient temperature, the remaining NaH is deactivated and the resulting mixture is diluted with pentane/ethyl acetate (by volume ration 1/1) and filtered through a bed of silica gel. The filtrate is washed with water. The organic layer is dried with anhydrous magnesium sulfate, filtered and evaporated in vacuo. Purification by flash chromatography (silica gel: pentane/ethyl acetate 9/1 v/v) yields the title compound (0.6 g, 52 % yield) as an colorless oil.

EXAMPLE 4

(a) 2,4,6-Tris(1-methyl-3-trifluoromethylpyrazol-5-yloxy)pyridine

A mixture of 4.8 g (36 mmol) 2,4,6-trifluoropyridine, 19.8 g (119 mmol) 5-hydroxy-1-methyl-3-trifluoromethylpyrazole and 18.1 g (131 mmol) potassium carbonate in 25 ml anhydrous sulfolane is stirred and heated to 80° C. over a period of 3 days. After cooling, the mixture is diluted with pentane/ethyl acetate (by volume ration 1/1) and filtered through a bed of silica gel. The filtrate is washed 10 times with water and the organic layer is dried over magnesium sulfate. After removal of the solvents, the residue is washed with isopropyl ether and 19.1 g (93 % yield) colorless crystals of melting point 130 0C are obtained.

(b) 2,6-Bis(1-methyl-3-trifluoromethylpyrazol-5-yloxy)-4-methoxypyridine

A 3 ml aliquot of a 25 % solution of potassium methylate (10 mmol) in dry methanol is added to a solution of 5.7 g (10 mmol) 2,4,6-tris-(1-methyl-3-trifluoromethylpyrazol-5-yloxy)pyridine in 20 ml anhydrous methanol. After 2 hours at ambient temperature, the reaction mixture is heated to reflux. The solvent is removed under reduced pressure and ethyl acetate is added to the residue. The mixture is washed with a 2 N sodium hydroxide solution. After drying and filtration of the organic layer, the solvents are removed and the residue is washed with diisopropyl ether and pentane. Colorless crystals (1.9 g, 43 % yield) of melting point 107° C. are obtained.

(c) 2-(1-Methyl-3-trifluoromethylpyrazol-5-yloxy)-4-methoxy-6-(2,2,3,3-tetrafluoropropyloxy)flyridine To a mixture of 2,2,3,3-tetrafluoropropan-1-ol (0.29 g, 2.2 mmol) in dry sulfolane (2 ml) is added NaH (60 % in oil, 0.09 g, 2.2 mmol) and 2,6-bis-(1-methyl-3-trifluoromethylpyrazol-5-yloxy)-4-methoxypyridine (0.8 g,1.8 mmol). After stirring at 110° C. for 3.7 h the mixture is cooled to ambient temperature. The resulting mixture is diluted with pentane/ethyl acetate (by volume ration 1/1) and filtered through a bed of silica gel. The filtrate is washed 10 times with water. The organic layer is dried with anhydrous magnesium sulfate, filtered and evaporated in vacuo. Purification by flash chromatography (silica gel: pentane/ethyl acetate 9/1 v/v) yields the title compound (0.72 g, 57 % yield) of m.p. 73–74° C.

EXAMPLE 5

(a) 3-Hydroxy-5-trifluoromethylthiophene
Method A
5A Ethyl 3-methoxy-3-trifluoromethylacrylate Cesium carbonate (132.8 g) was added to a mixture of ethyl 4,4,4-trifluoroacetoacetate (75.0 g) and dimethylformamide (400 ml). The reaction mixture was heated to 20° C. for 30 minutes. A mixture of methyl tosylate (83.4 g) and dimethylformamide (150 ml) was added to the resulting reaction mixture within 40 minutes. The mixture was heated for 3 hours and cooled to room temperature. Upon dilution with water (800 ml) the reaction mixture was extracted with diethyl ether three times. The combined organic phases were washed with water and dried. The mixture was concentrated and the residue distilled under reduced pressure to yield the product as a clear liquid (48.5 g, 60 %) with a boiling point of 62–70° C. at 12 mm.

5B Methyl (3-hydroxy-5-trifluoromethylthien-2-yl)-carboxylate

A solution of 1 M potassium hydroxide in methanol (30 ml) is added to a cooled mixture of 5A (4.6 g), methyl thioglycolate (2.46 g) and methanol (10 ml). The resulting reaction mixture was stirred for 24 hours at room temperature. Then the mixture was poured on ice and acidified with 6N sulfuric acid (pH=2). The mixture is extracted with diethyl ether twice. The combined organic phases were washed with water and dried. The mixture was concentrated and the residue is distilled under reduced pressure to yield the product as a clear liquid (3.4 g, 65 %) with a boiling point of 42–45 ° C. at 0.10 mm.

5C (3-Hydroxy-5-trifluoromethylthien-2-yl)-carboxylic acid

A mixture of 5B (2.38 g) and methanol (20 ml) was added to a stirred solution of sodium hydroxide (1.68 g) in water (20 ml). The reaction mixture was heated at reflux for 3 hours. The reaction mixture was cooled to room temperature and concentrated in vacuo. The concentrate was cooled to 5° C. and acidified with concentrated HCI (3.5 ml). The resulting suspension was stirred at 5° C. for 30 minutes. The solid was collected by filtration, washed with water, then dried in vacuo at 35–40° C. to give the free acid (1.45 g, 65 %).

5D 3-Hydroxy-5-trifluoromethylthiophen 5C (1.80 g) was slowly heated under argon. Evolution of gas was observed at 90° C. Heating was continued for additional 3.5 hours at 90° C. The resulting oil was distilled under reduced pressure (boiling point 70–74° C. at 4 mm) to yield 1.18 g (82 %) of compound 5D.

Method B
5E Methyl (3-benzyloxy-5-trifluoromethylthien-2-yl)-carboxylate

A mixture of 5B (5.0 g) and dimethylformamide (50 ml) is treated with sodium hydride (1.06 g). Benzylbromide (3.15 ml) was slowly added to the resulting reaction mixture and stirred at room temperature for 20 hours. The --reaction mixture was poured into water. The mixture was extracted with diethyl ether twice. The combined organic phases were washed with water, dried and concentrated in vacuo. The crude product was chromatographed (hexane / dichloromethane, 1/1) to give the product as a white solid (4.5 g, 64 %) with a melting point of 52–53.5 ° C.

5F (3-Benzyloxy-5-trifluoromethvlthien-2-yl)-carboxvlic acid

A mixture of 5E (3.80 g) and tetrahydrofuran (12 ml) was heated to reflux in 2N sodium hydroxide (12 ml) for 12 hours. Then the mixture was poured on ice and acidified with 6N sulfuric acid (pH=1–2). The mixture is extracted with diethyl ether twice. The combined organic phases were washed with water and dried. The mixture was concentrated and the residue is distilled under reduced pressure to yield the product as a white solid (3.22 g, 89 %) with a melting point of 142–144° C.

5G 3-Benzyloxy-5-trifluoromethylthiophen

A mixture of 5F (14.5 g) and quinoline (50 ml) was treated with copper powder (4.57 g) and heated to 150° C. The reaction mixture is heated for 25 minutes at 150° C. and cooled to room temperature. The mixture was filtered and washed with water. Aqueous quinoline was acidified with 6N HCI (pH=2) and extracted with diethyl ether twice. The combined organic phases were washed with water and dried. The mixture was concentrated and the residue was chromatographed to yield a yellow liquid (8.74 g, 71 %).

5D 3-Hydroxy-5-trifluoromethylthiorphen

A mixture of 5G (7.75 g) and tetrachloromethane (50 ml) was treated with iodotrimethylsilane (12.30 ml) and heated to 60° C. for 12 hours. The reaction mixture was stirred at room temperature for 12 hours. Water (50 ml) was added and the resulting reaction mixture was extracted with dichloromethane three times. The combined organic phases were washed with water and dried. The crude reaction mixture was eluted through hexane (100 g/silica gel) to remove benzyliodide and then with diethyl ether. The etheral phases were concentrated and distilled in vacuo to give the product (3.33 g, 74 %) having a boiling point of 65–66 ° C. at 4 mm.

(b) 4-Cyano-2,6-bis(5-trifluoromethylthienyl-3-oxy)pyridine

A mixture of 5D (14.6 g, 86.7 mmol) and NaH (60 % in oil, 3.47 g, 86.7 mmol) in dry sulfolane is stirred at 30° C. 2,6-Dichloro-4-cyanopyridine (5 g, 29 mmol) is added and the resulting mixture is heated to 90° C. for 1.75 h. After cooling, the reaction mixture is diluted with pentane/ethyl acetate (by volume ration 1/1) and washed 10 times with water and once with 1 N NaOH. The organic layer is dried with anhydrous magnesium sulfate, filtered and evaporated in vacuo. Purification by flash chromatography (silica gel: pentane/ethyl acetate 95/5 v/v) yields the title compound (8 g, 64 % yield) of m.p. 103–104° C.

(c) 4-Cyano-2-(5-trifluoromethylthienyl-3-oxy)-6-(2-methylbenzyloxy)pyridine

A mixture of 2-methylbenzylalcohol (0.79 g, 6.3 mmol) and NaH (60 % in oil, 0.1 g, 6.3 mmol) in dry sulfolane (7 ml) is stirred for 30 min at 50° C. After adding of 4-cyano- 2,6-bis(5-trifluoromethylthienyl-3-oxy)pyridine (2.5 g, 5.73 mmol), the mixture is heated for 7 h at 90° C. Further 0.1 equivalents of NaH and 2-methylbenzylalcohol are added and the reaction mixture is stirred for 3 h at 90° C. After cooling to ambient temperature, the reaction mixture is diluted with pentane/ethyl acetate (by volume ration 1/1) and washed 10 times with water. The organic layer is dried with anhydrous magnesium sulfate, filtered and evaporated in vacuo. Purification by flash chromatography (silica gel: pentane|ethyl acetate 95/5 v/v) yields the title compound (0.89 g, 44 % yield) of m.p. 78° C.

(d) 4-Cyano-6-hydroxy-2-(5-trifluoromethylthienyl-3-oxy)-pyridine

To a solution of 4-cyano-2-(5-trifluoromethylthienyl-3-oxy)-6-(2-methylbenzyloxy)pyridine (0.52 g, 1.33 mmol) in dichloromethane (10 ml) is added iodotrimethylsilane (0.246 ml, 1.73 mmol) at 0° C. under nitrogen. After 4 days at 0° C. the mixture is stirred for 5 h at ambient temperature. The reaction mixture is diluted with pentane/ethyl acetate (by volume ration 1/1) and washed with water and with 2 N hydrochloric acid. The organic layer is dried with anhydrous magnesium sulfate, filtered and evaporated in vacuo. Purification by flash chromatography (silica gel: pentane/ethyl acetate 9/1 v/v) yields the title compound (0.24 g, 63 % yield) of m.p. 192° C.

(e) (E)-4-Cyano-6-(4,4,4-trifluorobut-2-enyloxy)-2-(5-trifluoromethylthienyl-3-oxy)pyridine To a mixture of 4-cyano-6-hydroxy-2-(5-trifluoromethylthienyl-3-oxy)pyridine (0.19 g, 0.66 mmol), 4,4,4-trifluorobut-2-en-1-ol (0.082 ml, 0.79 mmol), triphenylphosphine (0.21 g, 0.79 mmol) in dry THF (5 ml) is added diethyl azodicarboxylate (0.125 ml, 0.79 mmol) and the mixture is stirred for 7 h at ambient temperature. The reaction mixture is diluted with pentane/ethyl acetate (by volume ration 1/1) and washed with 2 N hydrochloric acid, with 2 N NaOH and with concentrated sodium bicarbonate. The organic layer is dried with anhydrous magnesium sulfate, filtered and evaporated in vacuo. Purification by flash chromatography (silica gel: pentanelethyl acetate 95/5 v/v) yields the title compound (0.25 g, 58 % yield) of m.p. 60° C.

EXAMPLES 6–39

The compounds listed in TABLE 1 can be prepared by methods analogeous to those described in examples 1 to 5, and according to the methods described in the foregoing description.

TABLE 1

Compounds of formula Ia (Ia)

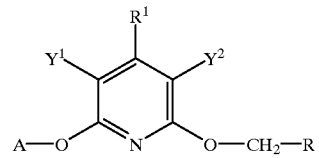

| Example | A | $Y^1$ | $Y^2$ | $R^1$ | R | m.p. [° C.] |
|---|---|---|---|---|---|---|
| 6 | 1-$CH_3$-3-$CF_3$-pyrazol-5-yl | H | H | $CH_3$ | —$CF_2CF_2H$ | 71 |
| 7 | 1-$CH_3$-3-$CF_3$-pyrazol-5-yl | H | H | $CH_3$ | —$C_2F_5$ | 53 |
| 8 | 1-$CH_3$-3-$CF_3$-pyrazol-5-yl | H | H | $CH_3$ | —$(CF_2)_3$—$CF_2H$ | oil |
| 9 | 1-$CH_3$-3-$CF_3$-pyrazol-5-yl | H | H | $CH_3$ | —$CH_2$—CBr=$CH_2$ | oil |
| 10 | 3-$CF_3$-phenyl | H | H | $CH_3$ | —CH=CH—$CF_3$ | oil |
| 11 | 1-$CH_3$-3-$CF_3$-pyrazol-5-yl | H | H | $CH_3$ | —CH=CCl—$CH_3$ | 61 |
| 12 | 1-$CH_3$-3-$CF_3$-pyrazol-5-yl | H | H | $CH_3$ | —CH=$CCl_2$ | 47 |
| 13 | 1-$CH_3$-3-$CF_3$-pyrazol-5-yl | H | H | $CH_3$ | —CCl=CHCl, (E) | oil |
| 14 | 1-$CH_3$-3-$CF_3$-pyrazol-5-yl | H | H | $CH_3$ | —CCl=CHCl, (Z) | oil |
| 15 | 1-$CH_3$-3-$CF_3$-pyrazol-5-yl | H | H | $CH_3$ | —CH=CHCl | oil |
| 16 | 1-$CH_3$-3-$CF_3$-pyrazol-5-yl | H | H | $CH_3$ | —CCl=CCl—$CH_3$ | oil |
| 17 | 1-$CH_3$-3-$CF_3$-pyrazol-5-yl | H | H | $CH_3$ | —CH=CH—$CCl_3$ | oil |
| 18 | 3-$CF_3$-phenyl | H | H | $CH_3$ | —$CF_2CF_2H$ | |
| 19 | 3-$CF_3$-phenyl | H | H | $CH_3$ | —$C_2F_5$ | |
| 20 | 3-$CF_3$-phenyl | H | H | $CH_3$ | —$(CF_2)_3$—$CF_2H$ | |
| 21 | 3-$CF_3$-phenyl | H | H | $CH_3$ | —CH=CCl—$CH_3$ | |
| 22 | 3-$CF_3$-phenyl | H | H | $CH_3$ | —CH=$CCl_2$ | |
| 23 | 5-$CF_3$-thien-3-yl | H | H | CN | —$CF_2CF_2H$ | |
| 24 | 5-$CF_3$-thien-3-yl | H | H | CN | —$C_2F_5$ | |
| 25 | 5-$CF_3$-thien-3-yl | H | H | CN | —$(CF_2)_3$—$CF_2H$ | |
| 26 | 5-$CF_3$-thien-3-yl | H | H | CN | —CH=CCl—$CH_3$ | |
| 27 | 5-$CF_3$-thien-3-yl | H | H | CN | —CH=$CCl_2$ | oil |
| 28 | 5-$CF_3$-thien-3-yl | H | H | CN | —CH=$CClCH_3$ | oil |
| 29 | 5-$CF_3$-thien-3-yl | H | H | CN | —CH=$CHCF_3$ | 60 |
| 30 | 3-$CF_3$-phenyl | H | H | $CH_3$ | —CH=$CClCH_3$ | oil |
| 31 | 1-$CH_3$-3-$CF_3$-pyrazol-5-yl | H | H | $CH_3$ | —C($CH_3$)=$CHCF_3$ | oil |
| 32 | 1-$CH_3$-3-$CF_3$-pyrazol-5-yl | H | H | $CH_3$ | —CH=C($CH_3$)$CF_3$ | oil |
| 33 | 1-$CH_3$-3-$CF_3$-pyrazol-5-yl | F | F | $CH_3$ | —CH=$CCl_2$ | 44 |
| 34 | 1-$CH_3$-3-$CF_3$-pyrazol-5-yl | F | F | $CH_3$ | —CH=CHCl | 73 |
| 35 | 1-$CH_3$-3-$CF_3$-pyrazol-5-yl | F | F | $CH_3$ | —CH=$CClCH_3$ | 66 |
| 36 | 1-$CH_3$-3-$CF_3$-pyrazol-5-yl | H | H | $CH_3$ | —CCl=$CH_2$ | 59 |
| 37 | 1-$CH_3$-3-$CF_3$-pyrazol-5-yl | H | H | $CH_3$ | —CH=CH—$CH_2Cl$ | oil |

TABLE 1-continued

Compounds of formula Ia

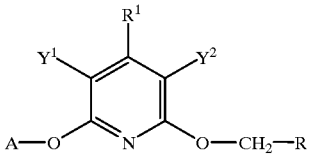

(Ia)

| Example | A | $Y^1$ | $Y^2$ | $R^1$ | R | m.p. [° C.] |
|---|---|---|---|---|---|---|
| 38 | 1-CH$_3$-3-CF$_3$-pyrazol-5-yl | H | H | CH$_3$ | —CH$_2$CF=CF$_2$ | |
| 39 | 1-CH$_3$-3-CF$_3$-pyrazol-5-yl | H | H | CH$_3$ | CH$_2$C(CH$_3$)=CF$_2$ | |

Herbicidal Activity Tests

1. Pre-emergence Herbicidal Evaluation of Test Compounds

The pre-emergence herbicidal activity of the compounds of the present invention is exemplified by the following test in which the seeds of a variety of monocotyledonous and dicotyledonous plants are seperately mixed with potting soil and planted on top of approximately one inch of soil in separate pots. After planting, the pots are sprayed with the selected aqueous acetone solution containing test compound in sufficient quantity to provide the equivalent of about 0.0125 to 0.4 kg per hectare of test compound per pot. The treated pots are then placed on greenhouse benches, watered and cared for in accordance with conventional greenhouse procedures. From 2 to 4 weeks after treatment, the tests are terminated and each pot is examined and rated according to the rating system set forth below.

| Rating System | % Difference in Growth Versus Untreated Control |
|---|---|
| 0 - No effect | 0 |
| 1 - Trace effect | 1–5 |
| 2 - Slight effect | 6–15 |
| 3 - Moderate effect | 16–29 |
| 4 - Injury | 30–44 |
| 5 - Definite injury | 45–64 |
| 6 - Herbicidal effect | 65–79 |
| 7 - Good herbicidal effect | 80–90 |
| 8 - Approaching complete kill | 91–99 |
| 9 - Complete kill | 100 |
| Plant Species Used | |
| GLXMA | *Glycine max* | soyabeans |
| HORVW | *Hordeum vulgare* | winter barley |
| ORYSA | *Oryza sativum* | rice |
| TRZAW | *Triticum aestivum* | winter wheat |
| ZEAMX | *Zea mays* | maize |
| ABUTH | *Abutilon theophrasti* | velvetleaf |
| AMBEL | *Ambrosia artemiisifolia* | ragweed |
| CASOB | *Cassia obtusifolia* | sicklepod |
| GALAP | *Galium aparine* | cleaver |
| IPOHE | *Ipomoea hederacea* | morning glory |
| LAMPU | *Lamium purpureum* | purple deadnettle |
| MATIN | *Matricaria inodora* | mayweed |
| SOLNI | *Solanum nigrum* | black nightshade |
| STEME | *Stellaria media* | chickweed |

-continued

| Rating System | % Difference in Growth Versus Untreated Control |
|---|---|
| ALOMY | *Alopecurus myosuroides* | black grass |
| DIGSA | *Digitaria sanguinalis* | large crabgrass |
| ECHCG | *Echinochloa grus galli* | barnyard grass |
| SETVI | *Setaria viridis* | green foxtail |

The herbicidal proficiency of the active ingredients of the present invention is evident from the test results which are recorded in Table A below.

Crop selectivity and weed control of compounds according to the invention 30 pre-emergence application The compounds of the invention showed good selectivity in maize up to e highest dose of 0.4 kg/ha. Furthermore, the compounds of the present vention displayed good selectivity in soybeans. At crop selective doses the mpounds of the present invention showed superior weed control. The results these tests are presented in Table A below.

Table A

Crop selectivity and weed control of compounds according to the vention in pre-emergence application—crop and weed species

TABLE A

Crop selectivity and weed control of compounds according to the invention in pre-emergence application - crop and weed species

| Example | Dose (kg/ha) | GLXMA | HORVW | ORYSA | TRZAW | ZEAMX | ABUTH | AMBEL | CASOB | GALAP | IPOHE | LAMPU | MATIN | SOLME | STEMY | ALOMY | DIGSA | ECHCG | SETVI |
|---------|--------------|-----|-----|-----|-----|-----|-----|-----|-----|-----|-----|-----|-----|-----|-----|-----|-----|-----|-----|
| 1 | 0.4 | 5 | 5 | 5 | 4 | 5 | 9 | 9 | 9 | 9 | 9 | 9 | 9 | 9 | 9 | 9 | | 9 | 9 |
| 1 | 0.1 | 4 | 5 | 4 | 3 | | 8 | 9 | 9 | 7 | 7 | 9 | 9 | 9 | 9 | 8 | | 7 | 9 |
| 1 | 0.025 | 1 | 2 | 2 | 1 | 2 | 7 | 9 | 9 | 2 | 5 | 9 | 9 | 8 | 9 | 6 | | 5 | 9 |
| 1 | 0.013 | 1 | 1 | 2 | 1 | 1 | 7 | 5 | 0 | 1 | 2 | 8 | 8 | 4 | 5 | 4 | | 3 | 9 |
| 2 | 0.4 | 4 | 5 | 3 | 3 | 4 | 9 | 9 | 9 | 9 | 7 | 9 | 9 | 9 | 9 | 9 | | 9 | 9 |
| 2 | 0.1 | | 3 | 2 | 1 | 2 | 6 | 8 | 9 | 2 | 3 | 9 | 8 | 8 | 9 | 7 | | 8 | 9 |
| 2 | 0.025 | 1 | 0 | 1 | 0 | 1 | 4 | 3 | 1 | 0 | 3 | 8 | 6 | 1 | 0 | 1 | | 2 | 6 |
| 2 | 0.013 | 0 | 0 | 0 | 0 | 0 | 1 | 1 | 0 | 0 | 1 | 8 | 4 | 0 | 0 | 1 | | 0 | 5 |
| 4 | 0.4 | 8 | 4 | 3 | 4 | 5 | 9 | 9 | 9 | 8 | 9 | 9 | 9 | 8 | 9 | 8 | | 8 | 9 |
| 4 | 0.1 | 6 | 3 | 2 | 1 | 3 | 7 | 9 | 7 | 5 | 9 | 9 | 9 | 8 | 9 | 8 | | 8 | 9 |
| 4 | 0.025 | 4 | 2 | 1 | 0 | 1 | 5 | 9 | 4 | 3 | 6 | 8 | 8 | 8 | 6 | 3 | | 5 | 8 |
| 4 | 0.013 | 1 | 1 | 1 | 0 | 1 | 3 | 4 | 3 | 1 | 3 | 8 | 8 | 6 | 4 | | | 3 | 5 |
| 6 | 0.4 | 5 | 3 | 2 | 2 | 5 | 9 | 9 | 9 | 8 | 8 | 9 | 9 | 9 | 9 | 9 | 9 | 9 | 9 |
| 6 | 0.1 | 3 | 2 | 1 | 1 | 3 | 3 | 9 | | 5 | 2 | 9 | 9 | 8 | 9 | 9 | 9 | 8 | 8 |
| 6 | 0.025 | 2 | 0 | 0 | 0 | 1 | 2 | 1 | | 1 | 1 | 7 | | 4 | | 3 | 2 | 3 | 6 |
| 6 | 0.013 | 0 | 0 | 0 | 0 | 0 | 1 | 1 | | 1 | 0 | 7 | | 4 | | 1 | 1 | 0 | 4 |
| 7 | 0.4 | 3 | 3 | 2 | 2 | 2 | 7 | 9 | | 2 | 5 | 9 | 9 | 9 | 8 | 9 | 8 | 7 | 8 |
| 7 | 0.1 | 2 | 2 | 1 | 1 | 0 | 1 | 6 | | 1 | 2 | 8 | 8 | 4 | 7 | 4 | 6 | 4 | 5 |
| 7 | 0.025 | 0 | 0 | 1 | 0 | 0 | 0 | 1 | | 0 | 1 | 6 | 3 | 1 | 5 | 1 | 1 | 1 | 2 |
| 7 | 0.013 | 0 | 0 | 0 | 0 | 0 | | | | 0 | | | 0 | 0 | | 0 | 0 | 0 | 2 |
| 8 | 0.4 | 4 | 4 | 1 | 3 | 2 | 9 | 8 | | 8 | 9 | 9 | 9 | 8 | 9 | 8 | 9 | 8 | 9 |
| 8 | 0.1 | 2 | 3 | 1 | 1 | 1 | 7 | 8 | | 6 | 9 | 9 | 9 | 8 | 9 | 7 | 9 | 6 | 9 |
| 8 | 0.025 | 1 | 1 | 0 | 0 | 1 | 1 | 7 | | 1 | 2 | 8 | 8 | 3 | 4 | 1 | 2 | 1 | 3 |
| 8 | 0.013 | 0 | 0 | 0 | 0 | 1 | 0 | 5 | | 1 | 2 | 8 | 8 | 1 | 1 | 1 | 1 | 1 | 1 |
| 11 | 0.4 | 4 | 6 | 3 | 4 | 5 | 9 | 9 | | 8 | 9 | 9 | 9 | 9 | 9 | 9 | 9 | 9 | 9 |
| 11 | 0.1 | 2 | 3 | 2 | 2 | 3 | 9 | 9 | | 6 | 8 | 8 | 9 | 8 | 9 | 9 | 9 | 8 | 9 |
| 11 | 0.025 | 1 | 3 | 1 | 2 | 2 | 7 | 9 | | 3 | 4 | 8 | 9 | 7 | 9 | 9 | 8 | 6 | 8 |
| 11 | 0.013 | 0 | 3 | 1 | 0 | 1 | 3 | 7 | | 1 | 2 | 5 | 9 | 5 | 8 | 6 | 8 | 4 | 7 |
| 12 | 0.4 | 4 | 8 | 3 | 6 | 5 | 9 | 9 | | 9 | 9 | 9 | 9 | 8 | 9 | 9 | 9 | 9 | 9 |
| 12 | 0.1 | 3 | 5 | 1 | 3 | 3 | 8 | 9 | | 8 | 9 | 9 | 9 | 8 | 9 | 9 | 9 | 8 | 9 |
| 12 | 0.025 | 2 | 4 | 0 | 2 | 2 | 7 | 8 | | 4 | 3 | 9 | 9 | 8 | 8 | 8 | 9 | 5 | 9 |
| 12 | 0.013 | 1 | 3 | 0 | 1 | 0 | 2 | 8 | | 1 | 2 | 8 | 8 | 5 | 6 | 3 | 9 | 3 | 5 |
| 28 | 0.4 | | 3 | | 1 | | 8 | | | | 1 | 8 | 9 | 8 | 9 | 9 | 9 | | |
| 28 | 0.1 | | 1 | | 0 | | 7 | | | | 0 | 8 | 9 | 8 | 9 | 8 | 9 | | |
| 28 | 0.025 | | 0 | | 0 | | 5 | | | | 0 | 5 | 9 | 4 | 9 | 3 | 3 | | |
| 35 | 0.12 | | | | 3 | | | | | | | | 9 | | 9 | 9 | | | 9 |
| 35 | 0.06 | | | | 3 | | | | | | | | 9 | | 9 | 9 | | | 9 |
| 35 | 0.04 | | | | 1 | | | | | | | | 9 | | 8 | 9 | | | 8 |
| 36 | 0.4 | | 5 | | 2 | | 8 | | | 8 | 9 | 9 | 9 | | 9 | 9 | 9 | | 9 |
| 36 | 0.1 | | 3 | | 2 | | 5 | | | 3 | 3 | 8 | 9 | | 9 | 8 | 9 | | 9 |
| 36 | 00.25 | | 2 | | 0 | | 5 | | | 0 | 2 | 7 | 7 | | 5 | 4 | 8 | | 9 |

The compounds of the invention were quite selective in soybeans (see Table A), particularly for the compounds of Examples 7 and 11. Furthermore, the compounds of the invention, as demonstrated by Examples 7 and 8, exhibited good selectivity in maize. Overall, the compounds of the invention displayed excellent weed control. Examples 1 and 11 show superior activity against Setaria, Abutilon and Stellaria.

2. Post-emergence Herbicidal Evaluation of Test Compounds

The post-emergence herbicidal activity of the compounds of the present invention is demonstrated by the following test, wherein a variety of monocotyledonous and dicotyledonous plants are treated with formulations prepared from solutions of the test compounds in acetone containing 0.4 % by weight of an alkylphenol/ethylene oxide condensate available under the trade mark TRITON X-155. These acetone solutions are diluted with water and the resulting formulations applied at dosage levels equivalent of about 0.03 to 0.4 kg per hectare of test compound per pot. After spraying the plants are placed on greenhouse benches and are cared for in the usual manner, commensurate with conventional greenhouse practices. From 2 to 4 weeks after treatment, the seedling plants are examined and rated according to the rating system provided above. A rating 0 indicates growth as untreated control, a rating 9 indicates death. The results of the test are set out in Table B below.

Table B

Crop selectivity and weed control of compounds according to the invention in post-emergence application

TABLE B

Crop selectivity and weed control of compounds according to the invention in post-emergence application

| Example | Dose (kg/ha) | GLXMA | HORVW | ORYSA | TRZAW | ZEAMX | ABUTH | AMBEL | CASOB | GALAP | IPOHE | LAMPU | MATIN | SOLMME | STELY | ALOMY | DIGSA | ECHCG | SETVI |
|---|---|---|---|---|---|---|---|---|---|---|---|---|---|---|---|---|---|---|---|
| 1 | 0.4 | 8 | 5 | 5 | 5 | 6 | 8 | 7 | 5 | 8 | 9 | 8 | 8 | 5 | 6 | 8 | 8 | 8 | 8 |
| 1 | 0.1 | 8 | 5 | 3 | 3 | 5 | 8 | 7 | 5 | 8 | 9 | 8 | 8 | 5 | 5 | 8 | 8 | 8 | 8 |
| 1 | 0.03 | 6 | 3 | 2 | 2 | 2 | 8 | 6 | 5 | 7 | 9 | 8 | 8 | 5 | 5 | 6 | 7 | 5 | 5 |
| 2 | 0.4 | 8 | 3 | 3 | 3 | 5 | 9 | 8 |   | 9 | 9 | 8 | 9 | 8 | 8 | 8 | 9 | 7 | 8 |
| 2 | 0.1 | 8 | 3 | 3 | 3 | 4 | 8 | 6 |   | 7 | 9 | 8 | 8 | 8 | 6 | 5 | 9 | 5 | 8 |
| 2 | 0.03 | 7 | 3 | 2 | 2 | 2 | 8 | 5 |   | 5 | 8 | 8 | 6 | 7 | 4 | 2 | 7 | 2 | 4 |
| 4 | 0.4 | 8 | 5 | 4 | 5 | 5 | 6 | 7 |   | 9 | 9 | 8 | 7 | 5 | 8 | 8 | 8 | 9 | 9 |
| 4 | 0.1 | 8 | 3 | 2 | 3 | 3 | 6 | 6 |   | 9 | 9 |   | 7 | 5 | 6 | 6 | 7 | 8 | 8 |
| 4 | 0.03 | 5 | 3 | 2 | 2 | 2 | 4 | 3 |   | 6 | 8 | 7 | 5 | 4 | 6 | 3 | 5 | 6 | 6 |
| 6 | 0.4 | 7 | 3 | 1 | 3 | 5 | 6 | 6 | 6 | 7 | 9 | 7 | 6 | 4 | 3 | 8 | 7 |   | 6 |
| 6 | 0.25 | 7 | 1 | 1 | 1 | 1 | 2 | 3 | 4 | 3 | 7 | 4 | 4 | 1 | 2 | 2 | 4 |   | 2 |
| 6 | 0.1 | 7 | 2 | 1 | 2 | 2 | 4 | 4 |   | 6 | 8 | 6 | 6 | 2 | 2 | 6 | 6 |   | 3 |
| 7 | 0.4 |   | 3 | 3 | 3 | 3 | 2 | 5 |   | 5 | 9 | 6 | 8 | 0 | 5 | 5 | 9 | 7 | 8 |
| 7 | 0.1 |   | 3 | 3 | 2 | 2 |   | 2 |   | 5 | 9 | 2 | 7 | 0 | 5 | 4 | 9 | 7 | 4 |
| 7 | 0.03 |   | 2 | 3 | 2 | 2 | 2 | 1 |   | 3 | 3 | 0 | 2 | 0 | 2 | 2 | 2 | 4 | 2 |
| 8 | 0.4 | 8 | 3 | 2 | 3 | 3 | 7 | 8 | 7 | 8 | 9 | 9 | 9 | 8 | 8 | 8 | 9 | 8 | 8 |
| 8 | 0.1 | 7 | 3 | 2 | 2 | 1 | 5 | 8 | 7 | 7 | 9 | 8 | 9 | 5 | 5 | 7 | 9 | 5 | 6 |
| 8 | 0.03 | 5 | 2 | 1 | 2 | 1 | 1 | 5 | 2 | 5 | 7 | 8 | 9 | 3 | 3 | 2 | 8 | 2 | 3 |
| 11 | 0.4 |   | 4 | 4 | 3 | 5 | 8 | 8 |   | 9 | 9 | 8 | 8 | 8 | 8 | 8 | 9 | 8 | 8 |
| 11 | 0.1 |   | 4 | 3 | 3 | 5 | 7 | 7 |   | 9 | 9 | 3 | 8 | 6 | 6 | 8 | 9 | 8 | 6 |
| 11 | 0.03 |   | 3 | 1 | 3 | 2 | 5 | 3 |   | 6 | 6 | 0 | 7 | 3 | 4 | 6 | 9 | 8 | 5 |
| 12 | 0.4 | 8 | 6 | 4 | 5 | 6 | 9 | 7 | 8 | 9 | 9 | 8 | 8 | 8 | 8 | 9 | 9 | 9 | 9 |
| 12 | 0.1 | 8 | 5 | 3 | 3 | 4 | 9 | 6 | 8 | 8 | 9 | 8 | 8 | 8 | 8 | 9 | 9 | 9 | 9 |
| 12 | 0.03 | 5 | 3 | 2 | 3 | 2 | 8 | 5 | 8 | 7 | 9 | 8 | 8 | 8 | 8 | 8 | 8 | 9 | 9 |

In post-emergence application the compounds of the invention are very selective in maize up to 25 g/ha, displaying good overall levels of performance against weeds (Table B). In barley the compounds of the invention, in particular examples 6, 7 and 8, are effective for both grass control such as Setaria virides and broad-leaved weed control at crop selective doses.

What is claimed is:

1. A compound of the formula (I)

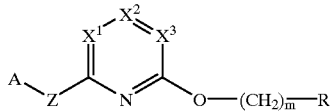

(I)

wherein $X^1$, $X^2$ and $X^3$ each represent $CR^1$;

$R^1$ each independently represent a hydrogen or halogen atom or an alkyl, alkenyl, alkynyl, alkoxy, alkoxyalkyl, alkoxyalkoxy group optionally substituted by one or more halogen nitro, cyano, hydroxyl, phenyl, $C_{1-4}$alkoxy $C_{1-4}$haloalkoxy, $C_{1-4}$haloalkylthio, or $C_{1-4}$alkoxycarbonyl; or a haloalkyl, haloalkoxy, cyano, nitro or $SF_5$ group; or -$S(O)_p$—$R^0$, in which p is 0, 1 or 2, and $R^0$ represents an alkyl or haloalkyl group; or -$NR^2R^3$, in which $R^2$ and $R^3$ each independently represent a hydrogen atom, an alkyl, alkenyl, aralkyl or aryl group, or $R^4$O—CY-, in which $R^4$ represents an alkyl group, and Y represents O or S;

A represents pyrazolyl group optionally substituted by one or more halogen nitro cyano amino hydroxyl $C_{1-4}$-alkyl $C_{1-4}$-alkoxy, $C_{1-4}$-haloalkyl, $C_{1-4}$-haloalkylthio, $C_{1-4}$-haloalkoxy $C_{2-4}$ haloalkenyl, or halosulfanyl groups having 1–5 halogen atoms;

R represents a haloalkyl or haloalkenyl group optionally substituted by one or more nitro, cyano, hydroxyl. alkoxy, haloalkoxy. alkoxycarbonyl or haloalkylthio groups;

m is 0, 1, 2 or 3;

Z represents an oxygen or sulfur atom;

and the agronomically acceptable salts or N-oxides thereof.

2. A compound as claimed in claim 1, wherein Z represents an oxygen atom.

3. A compound as claimed in claim 1, wherein R represents a group of formula 1:

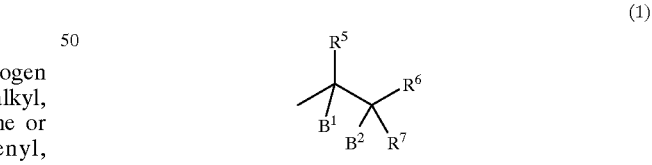

(1)

in which $R^5$ through $R^7$ represent a hydrogen or halogen atom or an optionally substituted alkyl or alkoxy group; at least one of which being a halogen atom, a haloalkyl or haloalkoxy group; and $B^1$ and $B^2$ each independently represent a hydrogen or halogen atom or taken together a double bond.

4. A compound of formula IA

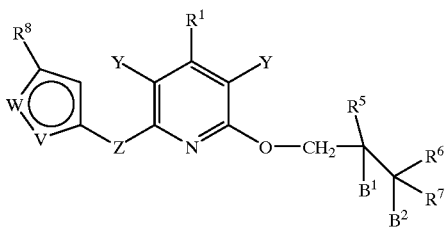

(IA)

wherein $R^1$ and Z have the meaning given in claim 1;

$R^5$ through $R^7$ each independently represent a hydrogen or halogen atom or an alkyl or alkoxy group optionally substituted by one or more halogen, nitro, cyano, hydroxyl, phenyl, $C_{1-4}$ alkoxy, $C_{1-4}$ haloalkoxy $C_{1-4}$ haloalkylthio or $C_{1-4}$ alkoxycarbonyl, at least one of $R^5$ through $R^7$ being a halogen atom, a haloalkyl or haloalkoxy group;

$R^8$ represents a halogen atom, or an alkyl grout optionally substituted by one or more halogen, nitro cyano, hydroxyl, phenyl, $C_{1-4}$ alkoxy, $C_{1-4}$ haloalkoxy, $C_{1-4}$ haloalkylthio or $C_{1-4}$ alkoxycarbonyl;

$B^1$ and $B^2$ each independently represent a hydrogen or halogen atom or taken together represent a double bond;

Y represents a hydrogen or fluorine atom; and

W-V represents N—$NCH_3$.

5. A compound according to clai selected from the group consisting of 2-(1-methyl-3-trifluoromethylpyrazol-5-yloxy)-6-(2,2, 3, 3-tetrafluoro-propyloxy)-4-methylpyridine;

2-(1-methyl-3-trifluoromethylpyrazol-5-yloxy)-6-(3-bromobut-3-enyloxy)-4-methylpyridine;

2-(1-methyl-3-trifluoromethylpyrazol-5-yloxy)-6-(4,4,4-trifluorobut-2-enyloxy)-4-methylpyridine;

2-(1-methyl-3-trifluoromethylpyrazol-5-yloxy)-6-(4,4,4-trifluorobut-1-enyloxy)-4-methylpyridine;

2-(1-methyl-3-trifluoromethylpyrazol-5-yloxy)-6-(3-chloroprop-2-enyloxy)-4-methylpyridine;

2-(1-methyl-3-trifluoromethylpyrazol-5-yloxy)-6-(2,2,3,3-tetrafluoropropyloxy)-4-methoxypyridine;

2-(1-methyl-3-trifluoromethylpyrazol-5-yloxy)-6-(2-methyl-4,4,4-trifluorobutyloxy)4-methylpyridine;

2-(1-methyl-3-trifluoromethylpyrazol-5-yloxy)-6-(3-methyl-4,4,4-trifluorobutyloxy)-4-methylpyridine;

6-(3,3-dichloroprop-2-enyloxy)-3,5-difluoro-2-(1-methyl-3-trifluoromethylpyrazol-5-yloxy)-4-methylpyridine;

3,5-difluoro-6-(3-chloroprop-2-enyloxy)-2-(1-methyl-3-trifluoromethylpyrazol-5-yloxy)-4-methylpyridine;

3,5-difluoro-6-(3-chlorobut-2-enyloxy)-2-(1-methyl-3-trifluoromethylpyrazol-5-yloxy)-4-methylpyridine;

6-(2-chloroprop-2-enyloxy)-2-(1-methyl-3-trifluoromethylpyrazol-5-yloxy)-4-methylpyridine;

6-(4-chlorobut-2-enyloxy)-2-(1-methyl-3-trifluoromethylpyrazol-5-yloxy)-4-methylpyridine;

2-(1-methyl-3-trifluoromethylpyrazol-5-yloxy)-4-methyl-6-(3,4,4-trifluorobut-3-enyloxy)-pyridine;

6-(4,4-difluoro-3-methylbut-3-enyloxy)-2-(1-methyl-3-trifluoromethylpyrazol-5-yloxy)-4-methylpyridine.

6. A herbicidal composition comprising at least one compound of general formula I, as claimed in claim 1, together with a carrier.

7. A composition as claimed in claim 6, comprising at least two carriers, at least one of which is a surface-active agent.

8. A method of combating undesired plant growth at a locus, comprising application to the locus of a compound of general formula I, as claimed in claim 1 or of a composition as claimed in claim 6.

\* \* \* \* \*